DENTAL INSTRUMENTS

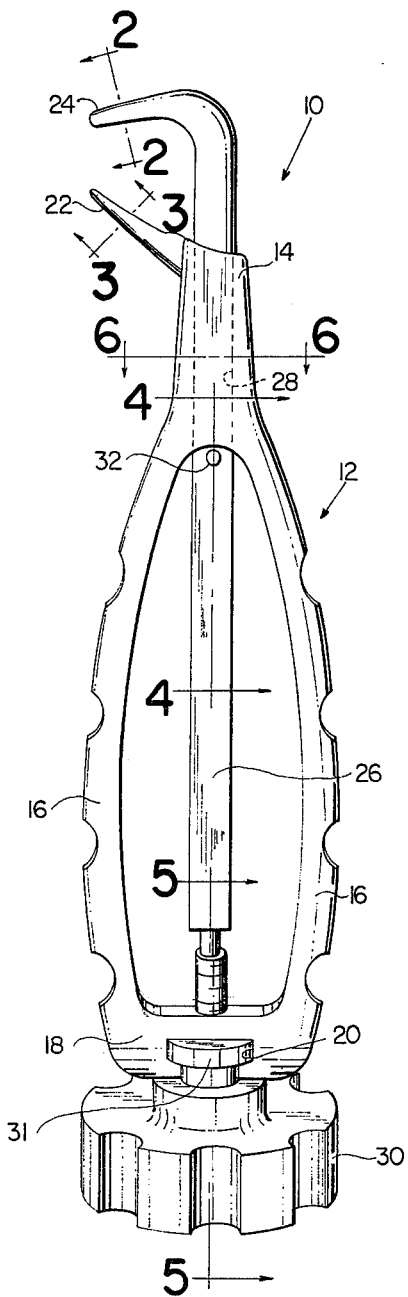
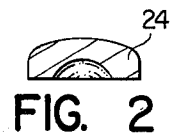
FIG. 2
FIG. 3
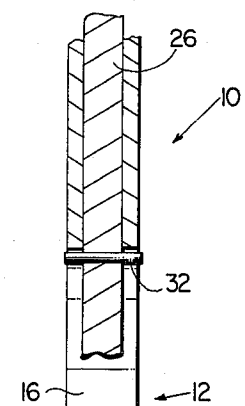
FIG. 4
FIG. 1
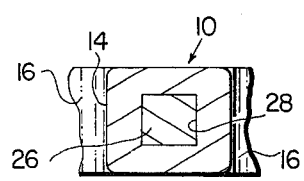
FIG. 6
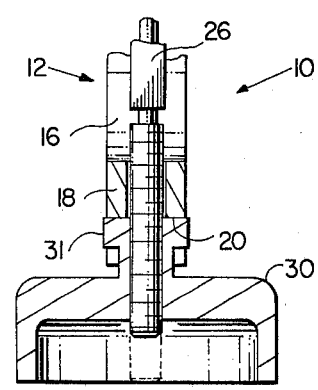
FIG. 5

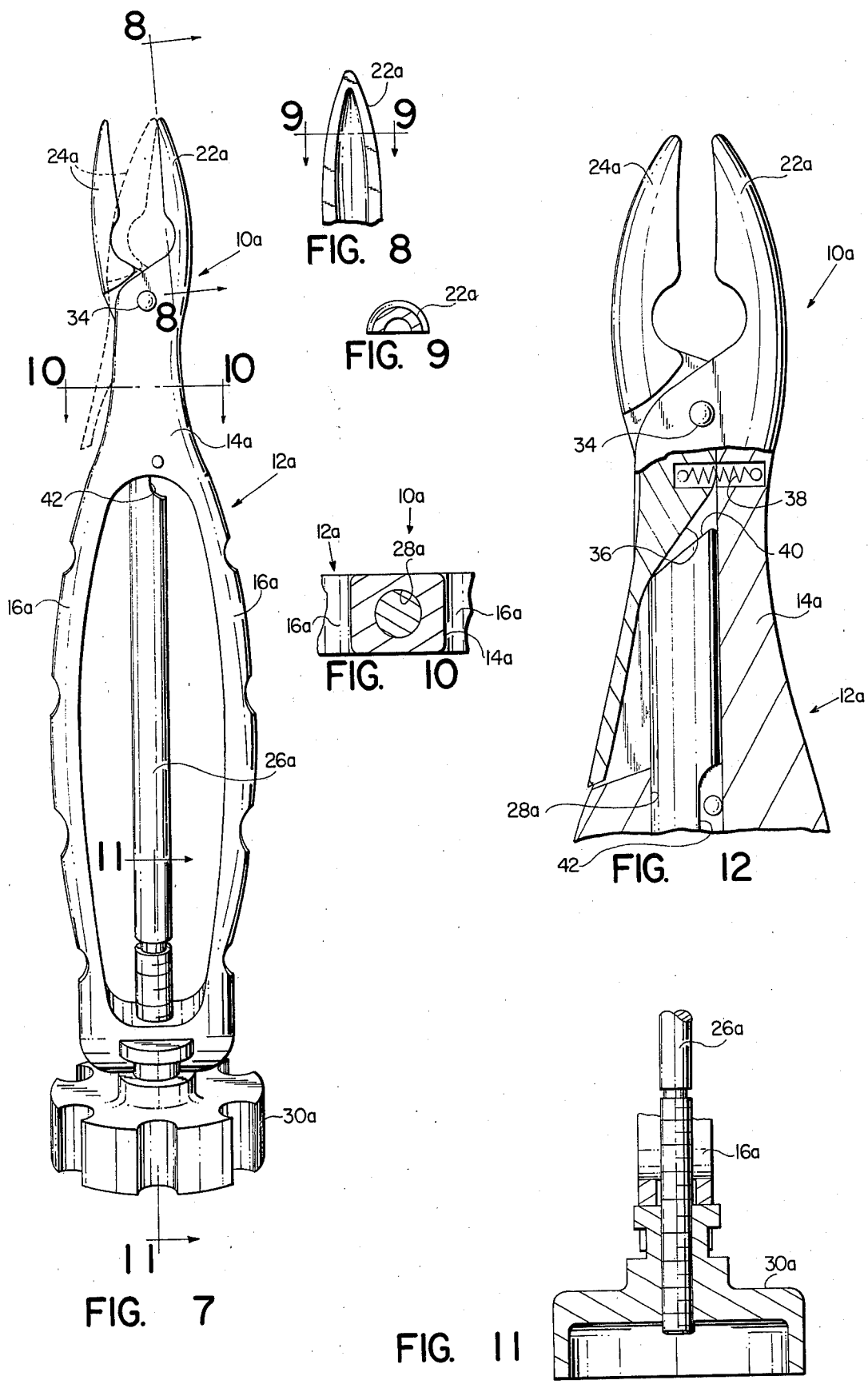

BACKGROUND OF THE INVENTION

This invention relates in general to dental instruments and deals more particularly with improved instruments of the type used in the extraction of teeth.

When a conventional dental forceps is used to extract a tooth the dental surgeon must apply considerable holding force to the forceps while simultaneously applying extracting force to the instrument. Any slipping or loosening of the grip on the tooth may cause the crown of the tooth to be broken off at or near the gum line, requiring surgical removal of the remaining portion of the tooth below the gum line. Excessive gum damage may also result. Premature release of the tooth after extraction may result in the tooth becoming lodged in the patient's esophagus or trachea or in his sinus area. The risk of such premature release is particularly severe when extraction is performed under general anethesia.

In order to overcome the aforesaid problems, dental instruments have been provided which clampingly engage a tooth during extraction. Such an instrument is shown and described in my U.S. Pat. No. 3,644,998 for Dental Instrument, issued Feb. 29, 1972. The instrument of the aforesaid patent has an elongated generally cylindrical handle which is rotated about its axis to effect clamping engagement of the beaks of the instrument with a tooth. It is the general aim of the present invention to provide improved clamping instruments of the aforedescribed general type.

SUMMARY OF THE INVENTION

In accordance with the invention a tooth extracting instrument includes an elongated handle which has a forward part and a pair of elongated arcuate grips integrally connected at their forward ends to the forward part. The grips are bowed outwardly and are integrally connected in spaced relation at their rear ends by a rear part which extends transversely between the rear ends of the grips. A first beak of the instrument is supported in fixed position on the forward part of the handle. A second beak is supported by the handle for movement generally toward and away from the first beak. An operating means for moving the second beak generally toward and away from the first beak includes an elongated operating rod which extends longitudinally of the handle in spaced relation to the grips and which is supported by the forward part and the rear part for longitudinal sliding movement relative thereto. Manually operable means is provided for moving the operating rod relative to the handle to move the first beak relative to the second beak and to maintain the beaks in selected position relative to each other.

BRIEF DESCRIPTION OF THE DRAWINGS

FIG. 2 is a somewhat enlarged fragmentary sectional view taken along the line 2—2 of FIG. 1.

FIG. 3 is a somewhat enlarged fragmentary sectional view taken along the line 3—3 of FIG. 1.

FIG. 4 is a somewhat enlarged fragmentary sectional view taken along the line 4—4 of FIG. 1.

FIG. 5 is a fragmentary sectional view taken along the line of 5—5 of FIG. 1.

FIG. 6 is a somewhat enlarged fragmentary sectional view taken along the line 6—6 of FIG. 1.

FIG. 7 is a perspective view of another tooth extracting instrument embodying the invention.

FIG. 8 is a somewhat enlarged fragmentary sectional view taken along the line 8—8 of FIG. 7.

FIG. 9 is a fragmentary sectional view taken along the line 9—9 of FIG. 8.

FIG. 10 is a somewhat enlarged fragmentary sectional view taken along the line 10—10 of FIG. 7.

FIG. 11 is a sectional view taken generally along the line 11—11 of FIG. 7.

FIG. 12 is a somewhat enlarged fragmentary longitudinal sectional view through a portion of the instrument shown in FIG. 7.

DETAILED DESCRIPTION OF PREFERRED EMBODIMENTS

Figure 1:
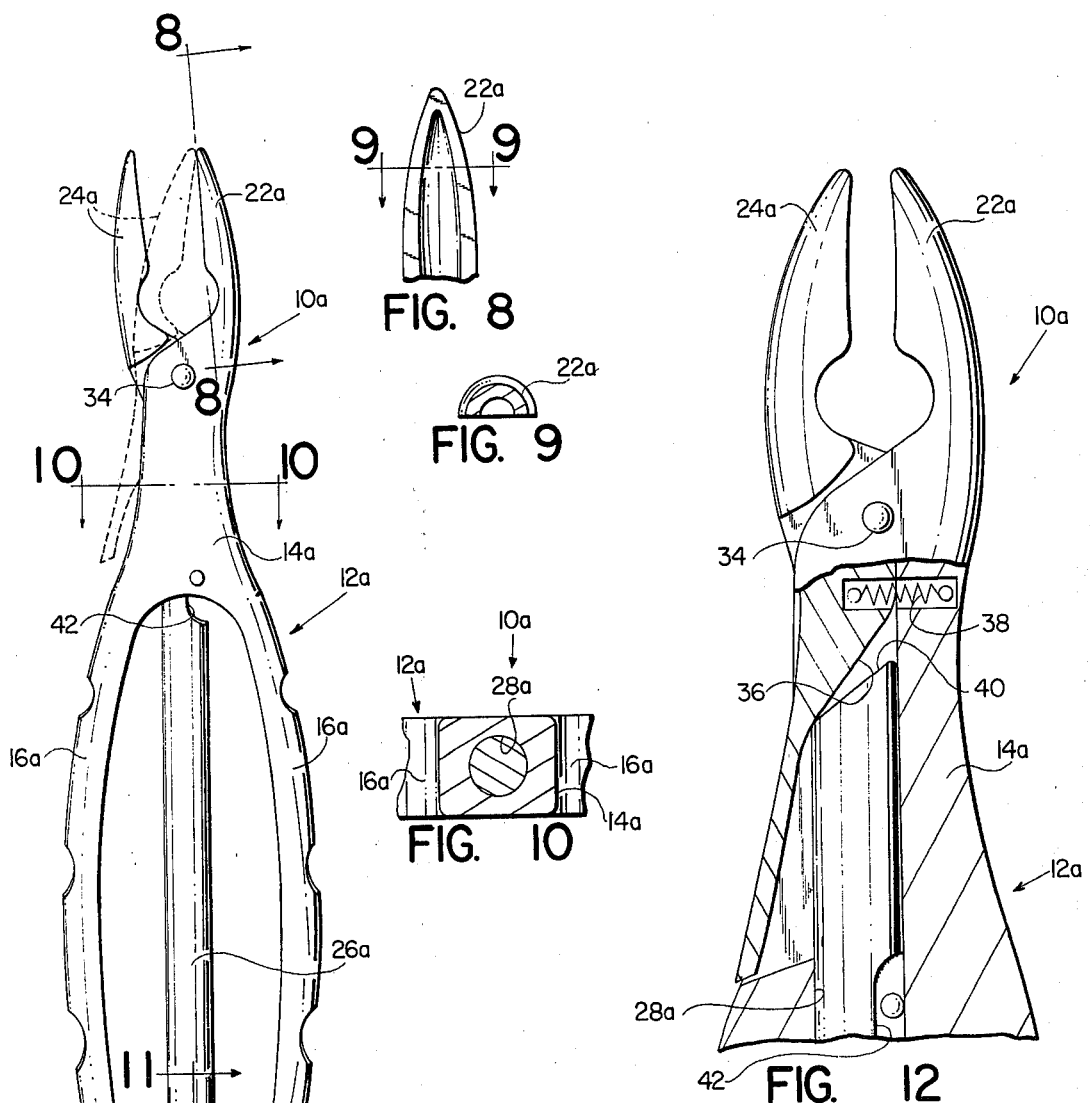
FIG. 1 is a perspective view of a tooth extracting instrument embodying the present invention.

Turning now to the drawings and referring first particularly to FIGS. 1-6, a dental instrument embodying the present invention is indicated generally by the reference numeral 10. The instrument 10 is particularly adapted for use in the extraction of a tooth and generally comprises an elongated handle designated by the numeral 12 which has a forward part 14. A pair of arcuately curved grips 16, 16 integrally connected to the forward part 14 extend rearwardly from it in spaced relation to each other. The handle 12 further includes a rear part 18 which is integrally connected to the rear end portions of the grips 16, 16 and which extends transversely between the grips. A rearwardly opening T slot 20 formed in the rear part 18 extends transversely through it, as best shown in FIG. 5.

The instrument 10 has a pair of beaks which includes a beak 22 supported in fixed position on the forward part 14. Preferably, and as shown, the beak 22 comprises an integral part of the handle 12 and projects in a transverse direction from the forward part 14. Another beak 24 is supported by the handle 12 for movement generally toward and away from the beak 22. Preferably, the beak 24 comprises an L-shaped end portion of an elongated operating rod 26 which extends longitudinally of the handle 12 in spaced relation to the grips 16, 16. The beaks 22 and 24 have opposing elongated recesses of arcuately contoured cross-section, as best shown in FIGS. 2 and 3, to conform generally to the anatomical contour of a tooth.

The operating rod 26 has a generally non-circular cross-section, at least at its forward end, and is slidably received within a passageway 28 which extends longitudinally through the forward part. The passageway has a non-circular cross-section which complements the cross-section of an associated forward part of the operating rod 26. The rear portion of the operating rod 26 is externally threaded, extends through a central opening in the rear part 18, and through and beyond the T slot 20, as best shown in FIG. 5.

A captive cylindrical nut 30 threadably engaged with the rear end portion of the operating rod 26 has a cylindrical forward end portion 31 of reduced diameter and generally T-shaped axial cross-section which is received within and retained by the T-slot 20. The peripheral surface of the nut 32 is preferably fluted, substantially as shown, to provide a substantially nonslip gripping surface.

A stop pin 32 extends transversely through the operating rod 26 and projects in opposite directions from it, substantially as shown in FIG. 4. The stop pin is positioned to engage the forward part 14 near the junction of the grips 16, 16 to limit forward travel of the operating rod 14 and its associated integral beak 24. Engagement of the stop pin 32 with the forward part 14 also serves to prevent disengagement of the nut 30 from the operating rod 26.

The non-traveling or captive nut 30 functions to move the beak 24 generally toward and away from the beak 22 and into or out of clamping relation with a tooth received therebetween. The unitary handle portion gives the instrument the "feel" of a conventional dental forceps and provides spaced apart gripping surfaces which enable effective control of the instrument without risk of slippage. The manually manipulated captive nut 30 retains the beaks 22 and 24 in clamping engagement with the tooth. Retention of the tooth by the beaks is not dependent upon force exerted upon the handle grips.

Referring now to FIGS. 7–12, another dental instrument embodying the present invention is indicated generally by the reference numeral 10a. The instrument 10a is similar in many respects to the instrument 10, previously described, and parts which correspond to previously described parts bear the same reference numerals and a letter "a" suffix and will not be hereinafter further described in detail. The instrument 10a differs from the instrument 10 primarily in the construction and arrangement of its beaks.

The illustrated instrument 10a is particularly adapted for use where an instrument having beaks which extend in a longitudinal direction relative to the axis of the instrument handle is required. Like the instrument 10, the instrument 10a has a beak 22a which is supported in fixed position on the forward part of the handle and which preferably comprises an integral part of the handle 12a. However, the beak 22a extends in a longitudinal direction relative to the handle 12a. The instrument 10a also has another beak 24a which is pivotally mounted on the forward part 14a by a pivot pin 34. The beaks 22a and 24a also have generally anatomically contoured arcuate tooth gripping surfaces, as previously described and as best shown in FIGS. 8 and 9 which illustrate a typical beak of the instrument. The beak 24a has a generally rearwardly facing cam surface 36 which is disposed rearwardly of the pivot pin 34 and which is inclined to the longitudinal axis of the handle 12a, substantially shown in FIG. 12. A biasing spring 38, concealed within the forward part 14a and the beak 24a acts between the movable beak 24a and the forward part of the handle to bias the movable beak to an open position away from the fixed beak 22a. The operating rod 26a is generally similar to the operating rod 26, previously described, but differs therefrom in that it has a generally circular cross-section throughout its length. The operating rod 26a also has a generally forwardly facing cam surface 40 at its forward end, which is inclined to the longitudinal axis of the operating rod, and a longitudinally extending recess 42 which opens through one side of the rod. The forward end portion of the operating rod 26a is slidably received within a passageway 28a which extends through the forward part 14a. The cam surface 40 is engageable with the cam surface 36 on the movable beak 24a. A stop pin 32a mounted in the forward part 14a extends across the passageway 28a and is engageable with abutment surfaces at opposite ends of the recess 42 to limit forward and rearward travel of the operating rod 26a in response to rotation of a captive nut 30a. The stop pin 32a also functions to prevent rotation of the operating rod about its longitudinal axis and relative to the handle 12a.

The beaks 22a and 24a are normally biased toward an open position by the spring 38. Rotation of the operating nut 30a in one direction causes coengagement of the cam surfaces 36 and 40 to move the beak 24a toward the beak 22a. The nut 30a cooperates with the operating rod 26a to releasably retain the movable beak 24a in fixed position relative to the fixed beak 22a whereby to maintain the instrument in clamped engagement with an associated tooth to be extracted.

I claim:

1. A tooth extracting instrument comprising a longitudinally extending unitary handle having a forward part and a pair of grips having forward end portions integrally connected in fixed relation to each other and to said forward part and extending rearwardly from said forward part in fixed spaced relation to each other, said handle having a rear part integrally connected in fixed relation to and extending transversely between the rear ends of said grips, a first beak supported in fixed position on said forward part, a second beak supported by said handle for movement generally toward and away from said first beak, and means for moving said second beak generally toward said first beak and including an elongated operating rod supported by said forward part and said rear part for longitudinal sliding movement relative to said handle and extending longitudinally of said handle between and in spaced relation to said grips, said operating rod extending through said rear part and having a rear portion extending rearwardly beyond said rear part, and manually operable means engaged with said rear portion of said operating rod and supported by said rear part for moving said operating rod relative to said handle, said manually operable means cooperating with said operating rod to maintain said first and second beaks in selected position relative to each other.

2. A tooth extracting instrument as set forth in claim 1 wherein each of said grips has a first portion defining said forward end portion and integrally connected to said forward part and curving transversely outwardly and rearwardly therefrom and a second portion integrally connected to said first portion and curving transversely inwardly and rearwardly therefrom and terminating at a junction with said rear part.

3. A tooth extracting instrument as set forth in either claim 1 or claim 2 wherein said manually operable means comprises a captive nut engaged in non-traveling relation with said rear part and threadably engaged with said operating rod.

4. A tooth extracting instrument as set forth in claim 3 wherein said rear part has a T-shaped slot formed therein and said captive nut includes a cylindrical portion having a T-shaped axial cross-section received within said T-shaped slot and retaining said nut in non-traveling engagement with said rear part.

5. A tooth extracting instrument as set forth in either claim 1 or claim 2 wherein said first beak is integrally connected to said forward part and projects in a transverse direction therefrom.

6. A tooth extracting instrument as set forth in claim 5 wherein said second beak is integrally connected to the forward end portion of said operating rod.

7. A tooth extracting instrument as set forth in claim 6 wherein said second beak is generally parallel to said first beak.

8. A tooth extracting instrument as set forth in claim 1 or claim 2 wherein said second beak is supported for pivotal movement on said forward part and relative to said first beak.

9. A tooth extracting instrument as set forth in claim 8 wherein said means for moving said second beak comprises coengaging cam surfaces on said operating rod and said second beak.

10. A tooth extracting instrument as set forth in claim 9 including means for biasing said second beak away from said first beak.

11. A tooth extracting instrument as set forth in claim 10 wherein said biasing means comprises a spring acting between said second beak and said forward part.

* * * * *